(12) United States Patent
Svanborg et al.

(10) Patent No.: US 6,599,874 B1
(45) Date of Patent: Jul. 29, 2003

(54) PROTEIN COMPLEX FROM ION-EXCHANGE CHROMATOGRAPHY OF CASEIN FOR TREATMENT OF BACTERIAL INFECTIONS

(76) Inventors: Catharina Svanborg, Arkivgatan 4, S-223 59 Lund (SE); H. Sabharwal, Bjorn Jansidas Gränd, S-224 77 Lund (SE)

( * ) Notice: Subject to any disclaimer, the term of this patent is extended or adjusted under 35 U.S.C. 154(b) by 0 days.

(21) Appl. No.: 09/639,938

(22) Filed: Aug. 17, 2000

Related U.S. Application Data (62) Division of application No. 08/793,047, filed as application No. PCT/SE94/00742 on Aug. 16, 1994, now abandoned.

(51) Int. Cl.$^7$ .................. A61K 38/00; A61K 47/00; A61K 38/17; A61K 35/20; A23C 23/00
(52) U.S. Cl. ................. 514/2; 426/580; 424/439; 424/442; 424/535; 530/360; 530/361; 530/365; 530/366
(58) Field of Search ................. 530/365, 366, 530/360, 361; 514/2, 21; 426/580; 424/439, 442, 635

(56) References Cited

U.S. PATENT DOCUMENTS

| | | | |
|---|---|---|---|
| 4,464,360 A | 8/1984 | Leffler et al. | 424/180 |
| 5,290,571 A | 3/1994 | Bounous et al. | 424/535 |
| 5,795,611 A | 8/1998 | Slattery | 426/580 |
| 5,968,901 A | * 10/1999 | Andersson et al. | 514/7 |

FOREIGN PATENT DOCUMENTS

| | | |
|---|---|---|
| EP | 0 022 696 | 1/1981 |
| EP | 0 339 656 | 11/1989 |
| FR | 2 671 697 | 7/1992 |

OTHER PUBLICATIONS

Heine et al., *J. Nutri.*, 121:277–283 (1990).
Kabara et al., *Antimicrobial Agents and Chemotherapy*, 2(1):23–28 (1972).
Gillin et al., *Science*, 221:1290–1292 (1983).
Herlea, *Revue Roumaine De Biologie*, 2(28):145–151 (1983).
Phillips et al., *Biochim. Biophy. Acta*, 229:407–410 (1971).
Prieels et al., *Biochimica et Biophysica Acta*, 491:76–81, 1977.
Nicholas et al., *Biochem. J.*, 194:149–154, 1981.
McKenzie et al., *J. Dairy Sci.*, 61:714–722, 1978.
Migliore–Samour et al., *Chem. Abstr.*,111:132334g, (1989).
Mitsubishi, *Chem. Abstr.*, 96:8094m, (1982).
Aniansson et al., *Microbial Pathogenesis*, 8:315–323 (1990).
Jenness et al., "Principles of Dairy Chemistry", John Wilry & Sons, Inc., pp. 121–127 (1959).

* cited by examiner

*Primary Examiner*—David M. Naff
(74) *Attorney, Agent, or Firm*—Burns, Doane Swecker & Mathis, LLP (57) ABSTRACT

Antibacterial protein complexes designated as Anti-adhesive Lactalbumin Like Protein (ALLP) are obtained by ion-exchange chromatography of casein and alpha-lactalbumin. Casein isolated from human milk by acid precipitation is subjected to ion-exchange chromatography using an NaCl gradient to obtain six fractions. Fraction six contains the antibacterial protein complex and is recovered. Ion-exchange chromatography of human or bovine alpha-lactalbumin using an NaCl gradient resulted in a fraction that was retained and eluted that contained an antibacterial multimeric protein complex. The protein complexes inhibit attachment of *S. pneumoniae* and *H. influenzae* to human respiratory tract epithelial cells when tested in vitro, and the protein complexes can be used to treat a bacterial infection in the respiratory tract. The protein complexes are administered in a pharmaceutical composition or in a food or feed-stuff.

13 Claims, 4 Drawing Sheets

PROTEIN COMPLEX FROM ION-EXCHANGE CHROMATOGRAPHY OF CASEIN FOR TREATMENT OF BACTERIAL INFECTIONS

This application is a division of application Ser. No. 08/793,047, filed Jul. 24, 1997, now abandoned, which is a 371 of PCT/SE94/00742, filed Aug. 16, 1994.

DESCRIPTION

Technical Field

The present invention relates to a novel antibacterial protein and compositions, in the form of pharmaceutical compositions, human food compositions, and animal feed-stuffs comprising said protein to be used in the therapeutic and/or prophylactic treatment of infections caused by bacteria, in particular *Streptococcus pneumoniae* and/or *Haemophilus influenzae*, as well as a method for diagnosing infections caused by said bacteria.

The object of the present invention is to obtain a protein and compositions containing said protein for prophylactic and/or therapeutic treatment of infections caused by bacteria, in particular *Streptococcus pneumoniae* and *Haemophilus influenzae* in the upper airways, ear-nose-and-throat infections, but also in the lower airways, e.g., the lungs by preventing adhesion of and/or causing a bactericidal effect on these bacteria. A further object is to be able to diagnose infections caused by these bacteria.

Background of the Invention

Natural antimicrobial compounds exist in secreted form as well as in cells of immune and non-immune origin.

Human milk has been used as a source for the purification of such compounds. These previously known compounds include specific antibodies to the micro-organism surface structure, casein, lysozyme, and oligosaccharides. The mechanism of action differs between the groups of antimicrobial molecules. Antibodies and receptor analogues prevent micro-organism adherence to mucosal surfaces. Lysozyme attacks the cell wall etc.

The term bacterial adherence denotes the binding of bacteria to mucosal surfaces. This mechanic association is a means for the organism to resist elimination by the body fluids, and to establish a population at the site where relevant receptors are expressed. In most cases where the mechanisms of attachment have been identified it is a specific process. The bacterial ligands, commonly called adhesins bind to host receptors. For Gram-negative bacteria, the adhesins are commonly associated with pili or fimbriae, rigid surface organelles that help bacteria to reach the appropriate receptor in the complex cell surface. The fimbriae function as lectins, i.e. they show specificity for receptor epitopes provided by the oligosaccharide sequences in host glyco-conjugates (13). For Gram-positive bacteria, on the other hand, the adhesins are not expressed as a surface organell, but rather linked to cell wall components and lipoteichoic acids (21,22). The receptor epitopes for Gram positive bacteria may consist of oligosaccharide sequences but can also be provided by peptides e.g. in connective tissue proteins (10).

The functional consequences of adherence depend on the virulence of the bacterial strain, and on the form of the receptor. When cell-associated, the ligand receptor interaction facilitates colonization and tissue attack (8). When secreted the receptor molecule will occupy the adhesins, and competitively inhibit attachment to the corresponding cell-bound receptor. Human milk is a rich source of such competing soluble receptor molecules.

The ability of specific antibodies to inhibit attachment is well established. This was first demonstrated for *Vibrio cholera* and oral streptococci. The anti-adhesive antibodies may act in either of two ways:

1) Antibodies to the receptor binding sites of the adhesin competitively inhibit receptor interaction or
2) antibodies to bacterial surface molecules which are not directly involved in adherence may agglutinate the bacteria and thereby reduce the number of organisms available for binding.

In either of the above cases the anti-adhesive activity of the antibody is attributed to the specificity of the antigen-combining site. Recently an alternative mechanism of interaction between secretory IgA and *E. coli* based on lectin-carbohydrate interactions was identified.

Human milk drastically inhibits the attachment of *Streptococcus pneumoniae* and *Haemophilus influenzae* to human nasopharyngeal epithelial cells. It contains antibodies to numerous surface antigens on these organisms, e.g., the phosphoryl choline and capsular polysaccharides of *S. pneumoniae*, the lipopolysaccharide and outer membrane proteins of *H. influenzae*. Accordingly, some of the anti-adhesive activity in milk resides in the immunoglobulin fraction.

The remaining anti-adhesive activity in the non-immunoglobulin fraction of milk may be explained by two types of molecules: free oligosaccharides and glycoproteins in the casein fraction.

Human milk is unique with regard to its content of complex carbohydrates. The free oligosaccharide fraction of milk is dominated by the lactoseries and with improving methods of isolation and characterization of carbohydrates more than 130 oligosaccharides containing up to 20 monosaccharides per molecule have been identified.

An anti-adhesive activity against *S. pneumoniae* in a low molecular weight fraction (<5 kDa) of milk was explained by the free oligosaccharides. In contrast there was no such effect against *H. influenzae* (15).

An anti-adhesive activity of high molecular weight components of milk was localized to the casein fraction. Human casein drastically reduced the adherence both of *S. pneumoniae* and *H. influenzae* (15). This effect was species specific.

Alpha-lactalbumin is a mettaloprotein, which shows some degree of heterogeneity depending on Ca(II) saturation and/or glycosylation (1). Alpha-lactalbumin acts as a specifier protein in the lactose synthase system. During lactation, alpha-lactalbumin is formed in the mammary gland and it alters the substrate specificity of the galactosyltransferase enzyme from N-acetyl glucosamine (GlcNAc) to glucose (Glc), enabling lactose synthesis to take place:

Multiple forms of bovine, pig, sheep and goat alpha-lactalbumin have been isolated and well characterized (2, 3). These multiple forms differ in a few amino residues or the number of disulphide bonds (4, 5) but are all active in the lactose synthase system. The physiological relevance or functions of these different forms of alpha-lactalbumin are not known. Alpha-lactalbumin has undergone a high rate of evulotionary change and it shows homology with lysozyme (1). These two proteins are thought to originate from the same ancestral protein. Whereas lysozyme is known as an anti-bacterial agent, alpha-lactalbumin has not yet been found to have anti-bacterial functions.

SUMMARY OF THE INVENTION

The present invention describes the identification of a new anti-bacterial protein or group of proteins from milk. The protein comprises a multimeric form of alpha-lactalbumin.

In the following this protein, or group of proteins, is abbreviated ALLP, Anti-adhesive Lactalbumin Like Protein.

The term antimicrobial or anti-bacterial protein used in the context of the present invention means here and in the following a protein which inhibits adherence of microorganisms to tissue and/or exerts a bactericidal effect on microorganisms.

Further characteristics of the invention will be evident from the accompanying claims.

BRIEF DESCRIPTION OF THE DRAWINGS

FIG. 1. The ion-exchange fractionation profile of casein (FIG. 1A) and commercial human alpha-lactalbumin (FIG. 1B). The arrow represents the time point at which 1 M NaCl was applied.

FIG. 2. Gel chromatographic fractionation profiles of pool VI obtained from fractionation of casein (FIG. 2A) and human alpha-lactalbumin before ion-exchange chromatography (FIG. 2B).

DETAILED DESCRIPTION OF THE INVENTION

The present invention will be described more in detail with reference to the example given below.

Experimental
Purification of the Active Anti-adhesive and Bactericidal Protein (ALLP)

Milk samples from lactating women were screened for anti-adhesive activity against *S. pneumoniae* and *H. influenzae*. About 50 l of breast milk with high anti-adhesive activity was collected from one healthy donor and used for the purification of ALLP. About 5 l of milk was thawed at a time and centrifuged to remove fat. Casein was prepared from the defatted milk by acid precipitation at pH 4.6. ALLP was purified as outlined below:

(i) Ion-exchange Chromatography of Casein

Figure 1A:
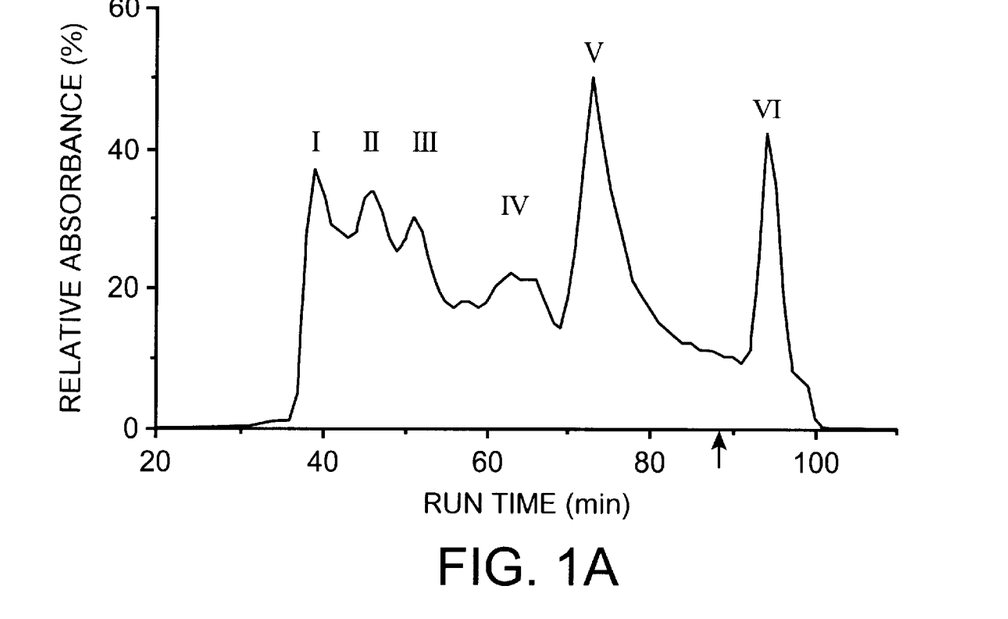

Casein was fractionated using an ion-exchange column (14 cm×1.5 cm) packed with DEAE-Tris-acryl M (LKB, Sweden) attached to an FPLC (Pharmacia, Sweden) using a NaCl gradient. 100 mg of the lyophilized casein was dissolved in 10 ml of 0.01 M Tris-HCl, pH 8.5. After centrifugation, the sample was directly applied to the column and the run was under the following conditions: buffer A: 0.01 M Tris-HCl, pH 8.5; Buffer B: buffer A containing 1 M NaCl/l. Gradient program: from 0–3 ml 100% A, from 3–60 ml 15% B; from 60–85 ml 25% B; from 85–87 ml 100% B; from 87–89 ml 100% B for 2 min; from 89–120 ml 100% A. The gradient was not linear, but was interrupted at the elution of each peak for better separation. Flow rate: 1 ml/min, recorder 0.2 cm/min. The buffers were degassed and filtered through a 0.22 um filter before use. The peaks were monitored at 280 nm and the fraction size was 3 ml. Fractions were pooled as shown (FIG. 1A). The pools (I–VI) were then desalted by dialysis (membrane cut off 3.5 kD) against distilled water for at least 48 hrs, lyophilized and tested for anti-adhesive activity.

Figure 2A:
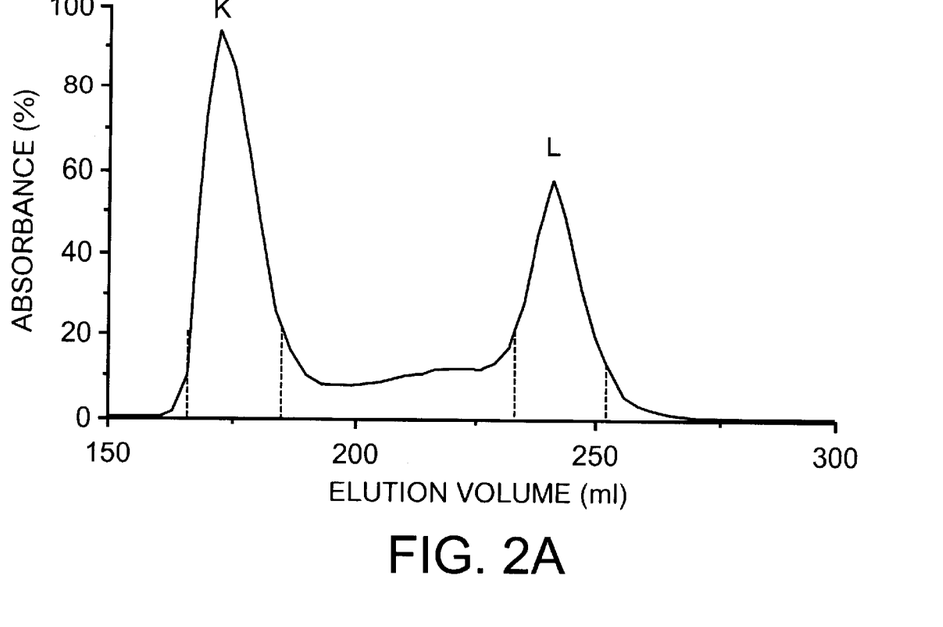

(ii) Gel Chromatography of Pool VI 100 mg of the active pool VI obtained after repeated FPLC fractionations of casein, were dissolved in 7 ml 0.06 M sodium phosphate buffer, pH 7.0 and applied to a Sephadex$^R$ G-50 (Pharmacia, Sweden) column (93 cm×2.5 cm). Flow rate was 30 ml/hr, peaks were monitored at 280 nm, 3 ml fractions were collected and pooled as shown (FIG. 2A). The pools were desalted by dialysis, lyophilized, tested for composition and for anti-adhesive activity.

Figure 1B:
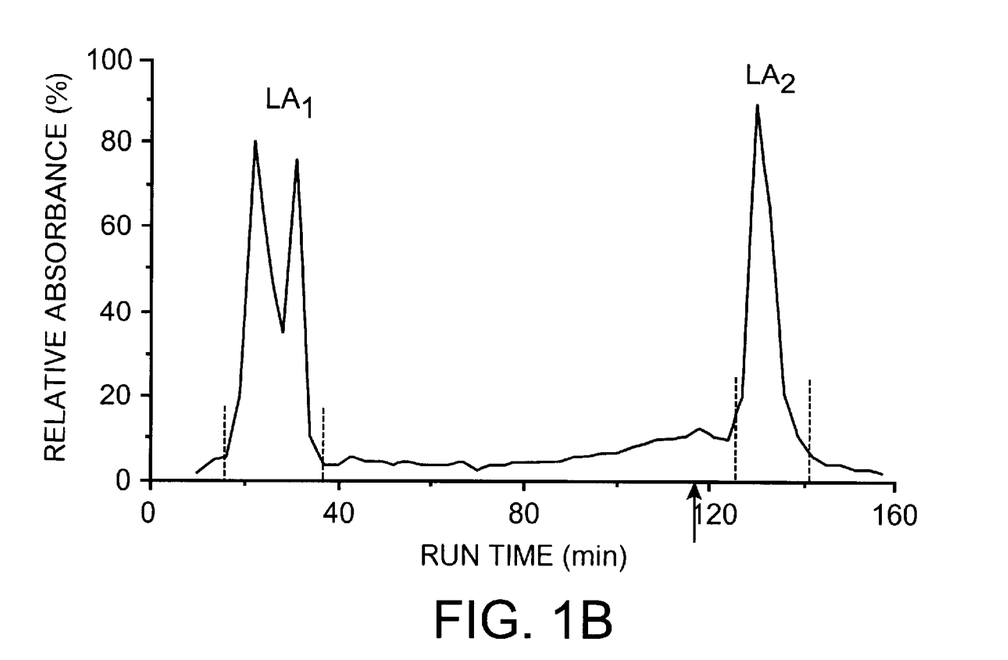

Ion-exchange Chromatography of Commercial Alpha-lactalbumin 20 mg of commercial (Sigma) human or bovine alpha-lactalbumin were dissolved in 2 ml 0.01 M Tris-HCl, pH 8.5. The ion-exchange chromatography of alpha-lactalbumin was under similar conditions as described above for the fractionation of casein. The NaCl gradient was linear (not interrupted), flow rate was 1 ml/min, 3 ml fractions were collected and pooled as shown in FIG. 1B. The pools were dialysed, (membrane cut-off 3.5 kD), lyophilized, resuspended to the required concentration and tested for anti-adhesive activity.

Gel Chromatography of Commercial Alpha-lactalbumin

Figure 2B:
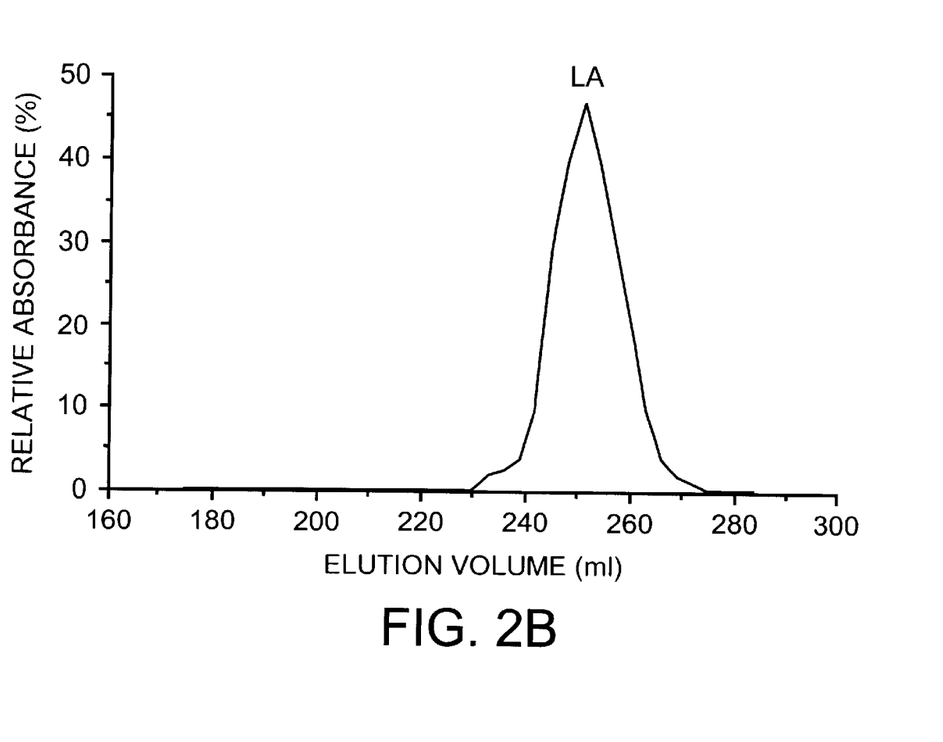
Figure 3:
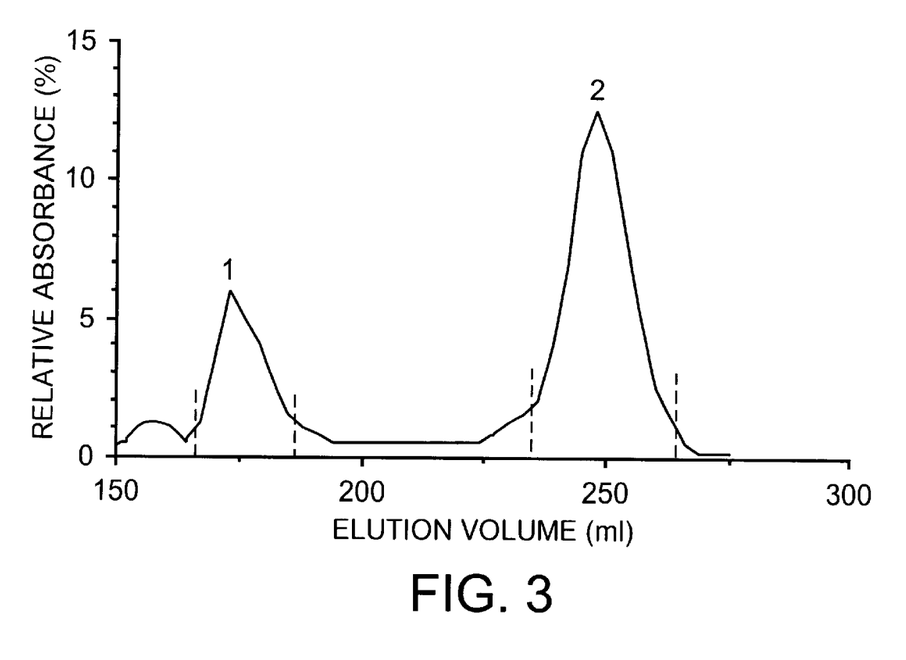
FIG. 3. Ion-exchange fractionation profile of pool $LA_2$ obtained after ion-exchange chromatography of alpha-lactalbumin.

Approximately 8–10 mg of commercial human or bovine alpha-lactalbumin (Sigma) were dissolved in 3 ml 0.06 M sodium phosphate buffer, pH 7.0 and fractionated on the Sephadex$^R$ G-50 column as described above. Flow rate was 30 ml/hr, peaks were monitored at 280 nm, 3 ml fractions were collected and pooled as shown (FIG. 2B). The pools were desalted by dialysis (membrane cut-off 3.5 kD) against distilled water for at least 48 hrs, lyophilized, tested for composition and for anti-adhesive activity. 6–8 mg retained of the material retained and eluting after 1 M NaCl during ion-exchange chromatography of alpha-lactalbumin were dissolved in 5 ml 0.06 M sodium phosphate buffer pH 7.0 and subjected to gel chromatography on the G-50 column as described above. 3 ml fractions were collected and pooled (FIG. 3). The pools were desalted, lyophilized, and tested for anti-adhesive activity.

Polyacrylamide Gradient Gel Electrophoresis (PAGGE)

Analytical PAGGE was Performed using 4–20% polyacrylamide pre-cast gels (Bio-Rad, Richmond, Calif.) on a Bio-Rad Mini Protean II cell. To 10 ul (5–10 mg/ml) each of the lyophilized fractions, an equal volume of sample buffer (13.1% 0.5 M Tris-HCl, pH 6.8, 10.5% glycerol. 1.2% SDS and 0.05%. bromophenol blue) was added. 20 ul of each was then loaded on to the gel which was run in Tris-glycine buffer (pH 8.3) with 0.1%SDS at 200V constant voltage for about 40 min. Staining of the proteins was made by immersing the gel in Coomassie Blue solution (0.1% in 40% methanol, 10% acetic acid) for about 0.5 hr. Destaining was by several changes in 40% methanol, 10% acetic acid until a clear background was obtained.

Ion Desorption Mass Spectrometry

ALLP and commercial alpha-lactalbumin were analyzed by ion-desorption mass spectrometry.

Bacteria

*S. pneumoniae* (CCUG3114 and 10175) and *H influenzae* (Hi198) were used throughout the experiments. These strains were known to adhere well to human nasopharyngal epithelial cells in vitro. These strains were initially isolated from the nasopharynx of children with frequent episodes of acute otitis media. The strains were kept lyophilized and were transferred to blood agar (10175) or Levinthal medium agar plates (Hi 198). *S. pneumoniae* was cultured for 9 hrs at 37° C. in liquid medium (17), harvested by centrifugation and suspended in 1 ml of 0.9% NaCl with 1% choline. *H. influenzae* Hi198 was cultured for 4 hrs in haemophilus medium (18), harvested by centrifugation and suspended in phosphate-buffer saline, (PBS).

Adhesion Inhibition

Adhesion and inhibition of adhesion was tested as previously described (15, 19). In brief, epithelial cells from the oropharynx of healthy donors ($10^5$/ml) were mixed with the bacterial suspensions ($10^9$/ml). After incubation of bacteria and epithelial cells, unbound bacteria were eliminated by repeated cycles of centrifugation and resuspension in NaCl with 1% choline (10175) or PBS (Hi 198).

The inhibitory activity of the different fractions was tested by preincubation with bacteria for 30 min at 37° C. prior to addition of epithelial cells. The number of epithelial cells attached was counted with the aid of an interference contrast microscope (Ortolux II microscope with interference contrast equipment TE Leitz, Wetzlar). Adherence was given as the mean number of bacteria/cell for 40 epithelial cells. Inhibition was given in percent of the value of the buffer control.

Results

Properties of ALLP

ALLP was purified from human milk by fractionation of casein by ion-exchange chromatography and fractionantion of the pool eluting after 1 M NaCl by gel chromatography. The ion-exchange fractionation profile of casein is shown in FIG. 1A. Eluted fractions were pooled as indicated and tested for anti-adhesive activity Pool VI retained the anti-adhesive activity of casein; this pool inhibited the attachment of *S. pneumoniae* and *H. influenzae* by more than 80% of the control (Table 3). The remaining fractions were inactive and were not analyzed further.

Pool VI was fractionated by gel chromatography on the Sephadex$^R$ G-50 column. The fractionation profile showed two distinct well separated peaks (FIG. 2A). Eluted fractions were pooled as show, desalted, and tested for anti-adhesive activity. Pool K retained 98% of the anti-adhesive activity against *S. pneumoniae* and 91% of the activity against *H. influenzae*. Pool L was inactive (Table 3).

Analytical PAGGE of pool K showed the presence of bands in the 14–15 kD region, one band in the 30 kD region, and two bands stained in the 100 kD region. Pool L showed the presence of only one band in the 14–15 kD region (FIG. 2A, inset). The N-terminal amino acid sequence analysis showed that the bands of pool K were similar and were identical to the N-terminal sequence of human alpha-lactalbumin. The active anti-adhesive protein in pool K was designated as Anti-adhesive Lactalbumin Like Protein (ALLP). ALLP reduced attachment of both *S. pneumoniae* and *H. influenzae* by about 60% at a concentration of 1 mg/ml.

Mass Spectrometry of ALLP

Figure 4:
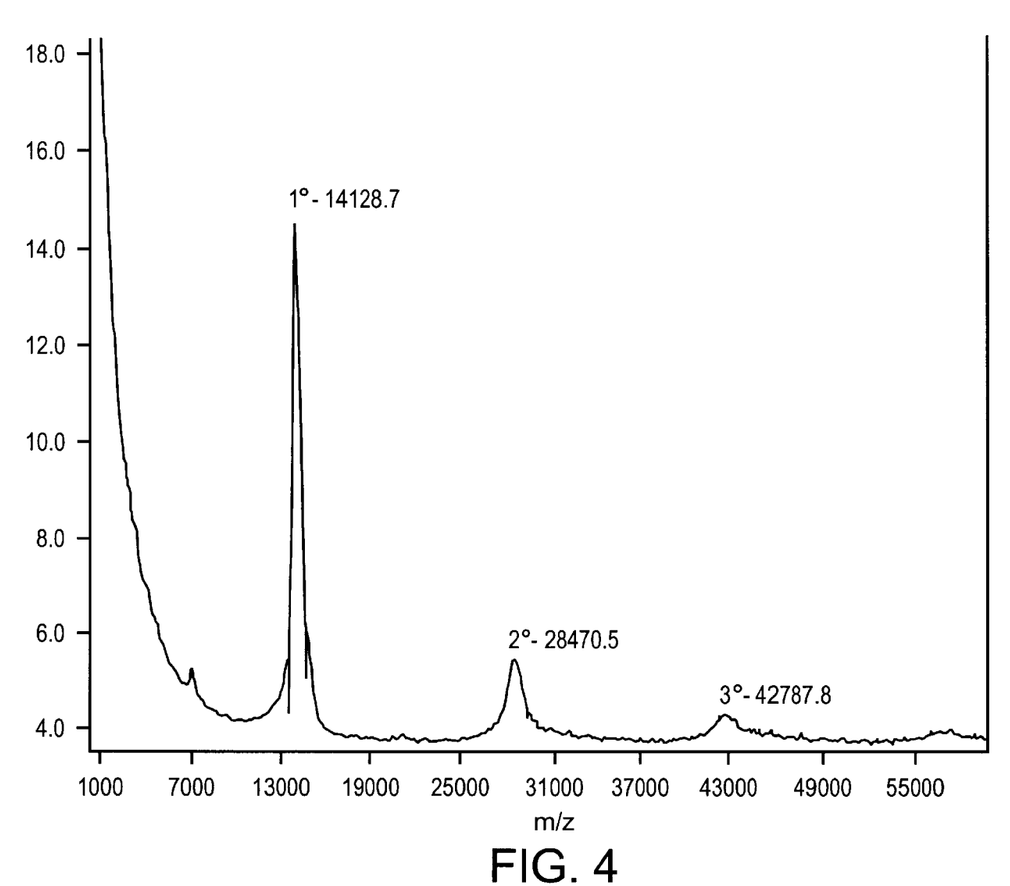
FIG. 4. Mass spectrometry of ALLP.

The results from analytical PAGGE suggested that ALLP might occur in a multimeric form. By ion laser desorption mass spectrometry, ALLP showed three distinct-mass fragments (1, 2 and 3) at 14128.7 m/z, 28470.5 m/z and 42787.8 m/z, respectively (FIG. 4). These fragments agreed with the monomeric (14 m/z), dimeric (28 m/z) and trimeric (42 m/z) mass ranges of the protein.

Comparison of ALLP and Commercial Alpha-lactalbumin

When tested for anti-adhesive activity, commercial alpha-lactalbumin did not inhibit the adherence of *S. pneumoniae* or *H. influenzae* even at a concentration of 10 mg/ml (Table 4). ALLP showed stained bands in the 14–15 kD, 30 kD and the 100 kD regions, whereas the commercial alpha-lactalbumin stained only one band in the 14–15 kD region. The N-terminal amino acid sequence of ALLP showed complete homology with the sequence of human alpha-lactalbumin.

The lack of anti-adhesive activity of commercial alpha-lactalbumin, as compared to ALLP, might be due to a difference in their molecular forms. Therefore commercial human alpha-lactalbumin was subjected to ion laser desorption mass spectrometry. The spectrum showed only one mass fragment at 14128.7 m/z corresponding to the monomeric form of alpha-lactalbumin (calculated molecular mass=14.079 kD). Thus commercial human alpha-lactalbumin was in the monomeric form and lacked anti-adhesive activity, whereas, ALLP was found to be multimeric and inhibited the attachment of *S. pneumoniae* and *H. influenzae* to human oropharyngeal cells in vitro.

Ion-exchange Chromatography of Human Alpha-lactalbumin

In order to test the effect of ion exchange chromatography on the anti-adhesive effect of commercial human alpha-lactalbumin, 20 mg of the commercial sample was applied onto the Tris-acryl column. The ion-exchange profile is shown in FIG. 1B. About 50% of the material applied was retained on the column and eluted after the application of 1 M NaCl (arrow, FIG. 1B). The different fractions were pooled as shown. After desalting and lyo-philization the fractions were reconstituted to a concentration of about 5–10 mg/ml and tested for anti-adhesive activity.

Anti-adhesive Effect of Human Alpha-lactalbumin After Ion-exchange Chromatography Before ion-exchange chromatography commercial human alpha-lactalbumin lacked anti-adhesive activity (Table 4). After it was subjected to ion-exchange chromatography, the pool which was retained and eluted with 1 M NaCl (pool $LA_2$, FIG. 1B) inhibited the attachment of both *S. pneumoniae* and *H. influenzae* by more than 95% of the value of the control (Table 4). The other pool ($LA_1$) obtained was inactive.

Gel Chromatography of Human Alpha-lactalbumin Before and After Ion-exchange Chromatography Since about 50% of the commercial human alpha-lactalbumin had become active after ion-exchange chromatography it was decided to check the mobility of the alpha-lactalbumin and pool $LA_2$ on gel chromatography.

The G-50 gel chromatographic profile of human alpha-lactalbumin before ion-exchange chromatography is shown in FIG. 2B. The alpha-lactalbumin eluted as a single peak, which gave a single band (14–15 kD) on PAGGE analysis (inset, FIG. 2B). This pool LA was found to be inactive when tested for anti-adhesive activity (Table 4).

The gel chromatographic profile of the active pool $LA_2$, obtained after ion-exchange chromatography of alpha-lactalbumin is shown in FIG. 3. This pool eluted as two well separated peaks (1 and 2, FIG. 3) corresponding to the eluting volumes of peaks K and L of the casein (FIG. 2A). When tested for anti-adhesive activity pool 1 retained the activity against both *S. pneumoniae* and *H. influenzae*, whereas pool 2 was inactive (Table 4).

When pool 1 was analysed by analytical PAGGE a pattern similar to that of ALLP was obtained, bands stained at 14–15 kD region, 30 kD region, and two bands at 100 kD region. Pool 2 gave a single band at the 14–15 kD region, corresponding to monomeric alpha-lactalbumin (inset, FIG. 3).

Properties of Commercial Bovime Alpha-lactalbumin

Since commercial human alpha-lactalbumin could be converted to the active multimeric form by ion-exchange chromatography it was decided to test the activity of bovine alpha-lactalbumin and to test its mobility on ion-exchange and gel chromatography. When tested for anti-adhesive activity, bovine alpha-lactalbumin was found to be inactive in inhibiting the attachment of S. pneumoniae and H. influenzae (Table 5).

20 mg of bovine alpha-lactalbumin were subjected to ion-exchange chromatography under similar conditions described above for human alpha-lactalbumin. 50% of the material applied to the column was retained and eluted after 1 M NaCl. The elution pattern was similar to that obtained for human alpha-lactalbumin (FIG. 1B). Pool $BL_2$ of bovine alpha-lactalbumin, corresponding to the elution volume of pool $LA_2$ of human alpha-lactalbumin (FIG. 1B) inhibited the attachment of S. pneumoniae by more than 95% and of H. influenzae by more than 80% of the value of the control (Table 5).

When subjected to gel chromatography on the G-50 column as described above, bovine alpha-lactalbumin eluted as a single peak corresponding to the elution volume of human alpha-lactalbumin (FIG. 2B). In contrast, the material in pool $BL_2$ resolved into two distinct peaks corresponding to pools 1 and 2 obtained for human alpha-lactalbumin (FIG. 3). The pool eluting just after the void volume of the column (corresponding to pool 1) retained the anti-adhesive activity, whereas, the other pool was inactive. The active pool had a PAGGE pattern similar to that of ALLP, whereas, the inactive pool stained only one band in the 14–15 kD region.

Thus a portion of the commercial bovine alpha-lactalbumin was also converted to the active multimeric form by ion-exchange chromatography.

Bactericidal Effect

The present ALLP was tested with regard to bactericidal effect on different strains of S. pneumoniae being known to be resistant to antibiotics, and some other strains of Streptococcus, E. coli, H. influenzae and M. cath.

Thereby the different bacterial strains were inoculated onto growth plates after incubation with ALLP in different concentrations. The viable counts (CFU) were determined at inoculation, 0.5 h, 2 h, and 4 h (hours), respectively, after inoculation. Table 1 below shows the viable counts after incubation to a medium containing 10 mg/ml of ALLP compared with the control.

TABLE 1

Viable counts (CFU) on S. pneumoniae strains after exposure to ALLP.

| Strain designation | | 0 h | 0.5 h | 2 h | 4 h |
|---|---|---|---|---|---|
| 10175 | control | $2 \times 10^6$ | $1 \times 10^6$ | $1 \times 10^5$ | $1 \times 10^4$ |
| | ALLP | $2 \times 10^5$ | — | — | — |
| 15006-92 | control | $1 \times 10^4$ | $2 \times 10^4$ | $1 \times 10^3$ | — |
| | ALLP | $2 \times 10^4$ | — | — | — |
| 14060-92 | control | $2 \times 10^6$ | $1 \times 10^5$ | $1 \times 10^4$ | — |
| | ALLP | $2 \times 10^5$ | — | — | — |
| 15256-92 | control | $1 \times 10^6$ | $2 \times 10^6$ | $2 \times 10^5$ | $4 \times 10^4$ |
| | ALLP | $2 \times 10^6$ | — | — | — |
| 14326-92 | control | $4 \times 10^5$ | $2 \times 10^5$ | $2 \times 10^4$ | $2 \times 10^3$ |
| | ALLP | $7 \times 10^4$ | — | — | — |
| Prag 1828 | control | $5 \times 10^6$ | $2 \times 10^6$ | $5 \times 10^5$ | — |
| | ALLP | $5 \times 10^6$ | — | — | — |
| 14091-92 | control | $3 \times 10^5$ | $5 \times 10^5$ | $1 \times 10^5$ | — |
| | ALLP | $7 \times 10^5$ | — | — | — |
| 14117-92 | control | $2 \times 10^6$ | $2 \times 10^6$ | $2 \times 10^6$ | — |
| | ALLP | $2 \times 10^6$ | — | — | — |
| 14612-92 | control | $3 \times 10^5$ | $1 \times 10^5$ | $2 \times 10^4$ | $1 \times 10^3$ |
| | ALLP | $3 \times 10^4$ | — | — | — |
| Dk 84/87 | control | $1 \times 10^7$ | $5 \times 10^6$ | $2 \times 10^6$ | $6 \times 10^4$ |
| | ALLP | $3 \times 10^5$ | — | — | — |

TABLE 1-continued

Viable counts (CFU) on S. pneumoniae strains after exposure to ALLP.

| Strain designation | | 0 h | 0.5 h | 2 h | 4 h |
|---|---|---|---|---|---|
| 14007-92 | control | $1 \times 10^5$ | $5 \times 10^4$ | $4 \times 10^3$ | — |
| | ALLP | $1 \times 10^5$ | — | — | — |
| 14030-92 | control | $5 \times 10^6$ | $2 \times 10^6$ | $2 \times 10^5$ | — |
| | ALLP | $5 \times 10^6$ | $2 \times 10^1$ | — | — |
| 14423-92 | control | $6 \times 10^5$ | $6 \times 10^6$ | $1 \times 10^6$ | $6 \times 10^5$ |
| | ALLP | $2 \times 10^5$ | $3 \times 10^1$ | — | — |
| 4502-93 | control | $4 \times 10^5$ | — | — | — |
| | ALLP | $5 \times 10^4$ | — | — | — |
| SA44165 | control | $2 \times 10^5$ | $5 \times 10^3$ | — | — |
| | ALLP | $3 \times 10^5$ | — | — | — |
| 1017-92 | control | $1 \times 10^6$ | $5 \times 10^5$ | $4 \times 10^3$ | — |
| | ALLP | $9 \times 10^5$ | — | — | — |
| 317-93 | control | $4 \times 10^4$ | $1 \times 10^4$ | $5 \times 10^3$ | — |
| | ALLP | $2 \times 10^3$ | — | — | — |
| 760-92 | control | $2 \times 10^7$ | $2 \times 10^6$ | $1 \times 10^4$ | $1 \times 10^4$ |
| | ALLP | $8 \times 10^6$ | — | — | — |
| Hun 859 | control | $6 \times 10^5$ | $3 \times 10^5$ | $2 \times 10^5$ | $2 \times 10^5$ |
| | ALLP | $3 \times 10^5$ | — | — | — |
| Hun 963 | control | $1 \times 10^7$ | $4 \times 10^6$ | $1 \times 10^5$ | — |
| | ALLP | $5 \times 10^6$ | — | — | — |
| BN 241 | control | $4 \times 10^6$ | $5 \times 10^4$ | $2 \times 10^4$ | — |
| | ALLP | $2 \times 10^5$ | — | — | — |

TABLE 2

Viable counts (CFU) on different bacterial species

| Strain designation | | 0 h | 0.5 h | 2 h | 4 h |
|---|---|---|---|---|---|
| S. mitis 116 | control | $1 \times 10^6$ | $10 \times 10^6$ | $2 \times 10^5$ | $1 \times 10^5$ |
| | ALLP | $1 \times 10^6$ | — | — | — |
| S. sanguis 197 | control | $5 \times 10^7$ | $3 \times 10^7$ | $4 \times 10^7$ | $5 \times 10^6$ |
| | ALLP | $3 \times 10^7$ | $2 \times 10^5$ | $2 \times 10^2$ | — |
| E. coli 60 | control | $6 \times 10^6$ | $5 \times 10^6$ | $-3 \times 10^6$ | $3 \times 10^6$ |
| | ALLP | $7 \times 10^6$ | $5 \times 10^6$ | $1 \times 10^7$ | $2 \times 10^7$ |
| 4 | control | $5 \times 10^6$ | $5 \times 10^6$ | $5 \times 10^6$ | $7 \times 10^6$ |
| | ALLP | $5 \times 10^6$ | $6 \times 10^6$ | $1 \times 10^7$ | $2 \times 10^7$ |
| H. influenzae 21594 | control | $4 \times 10^7$ | $1 \times 10^7$ | $4 \times 10^6$ | $2 \times 10^5$ |
| | ALLP | $3 \times 10^7$ | $4 \times 10^5$ | $<1 \times 10^3$ | $<1 \times 10^3$ |
| 21300 | control | $4 \times 10^7$ | $2 \times 10^7$ | $5 \times 10^6$ | $3 \times 10^5$ |
| | ALLP | $4 \times 10^7$ | $2 \times 10^6$ | $2 \times 10^4$ | $2 \times 10^3$ |
| M. cath. 71257 C+ | control | $4 \times 10^5$ | $3 \times 10^5$ | $5 \times 10^4$ | $2 \times 10^4$ |
| | ALLP | $3 \times 10^5$ | $2 \times 10^5$ | $3 \times 10^3$ | — |
| 71295 C+ | control | $2 \times 10^7$ | $1 \times 10^7$ | $3 \times 10^6$ | $6 \times 10^5$ |
| | ALLP | $2 \times 10^7$ | $5 \times 10^6$ | $2 \times 10^6$ | $3 \times 10^5$ |

C+ = beta-lactamase producing

A dose response curve was made up based on the bactericidal effect on S. pneumoniae 10175 at different levels of administration of ALLP compared with control (no addition). Thereby ALLP was administered at 0.1 mg/ml, 0.5 mg/ml, and 1.0 mg/ml, respectively. As little as 0.1 mg/ml of ALLP provides a bactericidal effect on S. pneumoniae.

The viable counts were further determined using different control proteins, viz. bovine serum albumine (BSA), alphalactal-bumine (bovine origin), lactoferrin (bovine origin) in a concentration of 10 mg/ml, and control (no protein). These proteins had no bactericidal effect on S. pneumoniae 10175.

A new form of alpha-lactalbumin (ALLP) with anti-adhesive activity and bactericidal effect against the respiratory tract pathogens S. pneumoniae and H. influenzae was thus isolated and characterized from a human milk sample. Commercial human or bovine alpha-lactalbumin lacked anti-adhesive activity in the assay system. A portion of the commercial human and bovine alpha-lactalbumin was converted to active form by ion exchange chromatography. The active and non-active forms of alpha-lactalbumin showed different mobilities on gel chromatography and their staining patterns on gel electrophoresis were also different. By ion-desorption mass spectrometry analysis, ALLP was found to be in the trimeric form, whereas commercial alpha-lactalbumin was monomeric. The activated forms of commercial human and bovine alpha-lactalbumin showed gel pattern similar to the trimeric form. A portion of the monomeric form of alpha-lactalbumin was separated from the multimeric form and was found to be inactive in inhibiting the adherence of both S. pneumoniae and H. influenzae. The three forms of alpha-lactalbumin (mono, di and tri) existed in some sort of equilibrium after ion-exchange chromatography and could not successfully be separated from each other. This proposes that the active anti-adhesive alpha-lactalbumin (ALLP) is a multimeric form not previously identified in human milk.

The identification of ALLP in a previous casein preparation was a result of its purification being monitored by the biological activity (16). It retained all of the anti-adhesive activity of casein and thus could be followed during the purification procedures. This form of alpha-lactalbumin has not previously been disclosed to be present in human milk. The early studies of the present inventors showed that the anti-adhesive effect of human milk against S. pneamoniae and H. influenzae was independent from the specific antibody activity and was concentrated in a casein fraction (15). Casein was, however, found to have both a bactericidal effect and an anti-adhesive effect. A bactericidal effect was present and was found to be more pronounced against S. pneumoniae than H. influenzae. The anti-adhesive activity remained intact aster removal of the fatty acids from casein. The mechanism of adhesion inhibition of ALLP was found to be independent from its carbohydrate content. Carbohydrate analysis of ALLP showed the presence of only one monosaccharide unit associated with the molecule. Removal of this monosaccharide unit by glucosidase treatment did not alter the anti-adhesive effect of ALLP. Also since the commercial forms of human and bovine alpha-lactalbumin could be activated by ion-exchange chromatography, it is very unlikely that the carbohydrate play any role in the anti-adhesive or bactericidal effect of ALLP tested by the biological analysis system.

Being predominantly a whey protein, alpha-lactalbumin is usually purified from the alpha-lactalbumin rich fractions of whey. Since the monomeric form and the multimeric forms have different mobilities on gel chromatography, the active multimeric forms are lost during the purification procedures. It is thus not surprising that the commercial preparations of alpha-lactalbumin lacked anti-adhesive properties in the present system. Genetic variants of alpha-lactalbumin have been isolated from milk of other mammals including bovine. Most of these forms consist of four disulphide bonds and a form of bovine alpha-lactalbumin with three disulphide bonds have also been isolated (5). The physiological role of these different forms of alpha-lactalbumin is not known. The present data demonstrate that the monomeric alpha-lactalbumin completely lacked biological activity in the present system. Aggregation and polymerization may therefore be an important event in the anti-adhesive activity of ALLP against S. pneumoniae and H. influenzae.

The present data demonstrate that the multimeric alpha-lactalbumin is active in adhesion inhibition of the respiratory tract pathogens and can thus play a role in the protection against respiratory and gastro-intestinal infections. It is also active as a bactericide on at least S. pneumoniae, even those being resistant to antibiotics.

Comments

S. pneumoniae and H. influenzae are important causes of morbidity and mortality in all age groups. Respiratory tract infections, e.g., meningitis, otitis, and sinusitis are caused by bacteria which enter via the nasopharynx. Colonization at that site may thus be an important determinant of disease (18). The finding that a specific alpha-lactalbumin derived from human as well as bovine milk inhibits attachment of both species opens the possibility to prevent colonization by specific interference of attachment using these structures. The bactericidal effect is hereby of importance as well.

The importance of the antimicrobial molecules is shown by the protection against infections which is seen in breast-fed babies. Breast-fed babies have a reduced frequency of diarrhoea, upper respiratory tract infections and acute otitis media (AOM). The bacterial species discussed in this application are the most frequent bacterial causes of AOM, viz. Haemophilus influenzae and Streptococcus pneumoniae.

As evident from the data shown the alpha-lactalbumin obtained from the human or bovine milk inhibits the attachment of S. pneumoniae and H. influenzae to human respiratory tract epithelial cells in vitro.

TABLE 3

Bacterial adhesion to oropharyngeal cells after incubation with active human milk, casein, and casein fractions obtained after ion-exchange chromatography on DEAE-Trisacryl

| | Adhesion | | | |
| --- | --- | --- | --- | --- |
| | S. pneumoniae | | H. influenzae | |
| Sample | Mean | (%) | Mean | (%) |
| Saline control | 150 | (100) | 200 | (100) |
| Human milk | 25 | (17) | 70 | (35) |
| Casein | 4 | (3) | 10 | (5) |
| Pool VI | 14 | (9) | 22 | (11) |
| Pool K | 3 | (2) | 17 | (9) |
| Pool L | 150 | (100) | 178 | (89) |

TABLE 4

Bacterial adhesion to oropharyngeal cells after incubation with human alpha-lactalbumin and the fractions obtained after ion-exchange chromatography and gel chromatography.

| | Adhesion | | | |
| --- | --- | --- | --- | --- |
| | S. pneumoniae | | H. influenzae | |
| Sample | Mean | (%) | Mean | (%) |
| Saline control | 138 | (100) | 130 | (100) |
| Human alpha-lactalbumin | 124 | (90) | 110 | (85) |
| Pool LA$_2$ | 4 | (3) | 9 | (7) |
| Pool LA | 128 | (93) | 76 | (58) |

TABLE 5

Bacterial adhesion to oropharyngeal cells after incubation with bovine alpha-lactalbumin and the fractions obtained after ion-exchange chromatography and gel chromatography.

| | Adhesion | | | |
| --- | --- | --- | --- | --- |
| | S. pneumoniae | | H. influenzae | |
| Sample | Mean | (%) | Mean | (%) |
| Saline control | 138 | (100) | 130 | (100) |
| Bovine alpha-lactalbumin | 130 | (94) | 99 | (76) |
| Pool BL$_2$ | 3 | (2) | 18 | (14) |

APPLICATIONS

The alpha-lactalbumin of the present invention can be administered in the form of an oral mucosal dosage unit, an 
injectable composition, or a topical composition. In any case the protein is normally administered together with commonly known carriers, fillers and/or expedients, which are pharmaceutically acceptable.

In case the protein is administered in the form of a solution for topical use the solution contains an emulsifying agent for the protein together with an diluent which can be sprayed into the nasopharynx, or can be inhaled in the form of a mist into the upper respiratory airways.

In oral use the protein is normally administered together with a carrier, which may be a solid, semi-solid or liquid diluent or a capsule. These pharmaceutical preparations are a further object of the present invention. Usually the amount of active compound is between 0.1 to 99% by weight of the preparation, preferably between 0.5 to 20% by weight in preparations for injection and between 2 and 50% by weight in preparations for oral administration.

In pharmaceutical preparations containing a protein of the present invention in the form of dosage units for oral administration the compound may be mixed with a solid, pulverulent carrier, as e.g. with lactose, saccharose, sorbitol, mannitol, starch, such as potatoe starch, corn starch, amylopectin, cellulose derivatives or gelatine, as well as with an antifriction agent such as magnesium stearate, calcium stearate, polyethylene glycol waxes or the like, and be pressed into tablets. Multiple-unit-dosage granules can be prepared as well. Tablets and granules of the above cores can be coated with concentrated solutions of sugar, etc. The cores can also be coated with polymers which change the dissolution rate in the gastrointestinal tract, such as anionic polymers having a $pk_a$of above 5.5. Such polymers are hydroxypropylmethyl cellulose phtalate, cellulose acetate phtalate, and polymers sold under the trade mark Eudragit S100 and L100.

In the preparation of gelatine capsules these can be soft or hard. In the former case the active compound is mixed with an oil, and the latter case the multiple-unit-dosage granules are filled therein.

Liquid preparations for oral administration can be present in the form of syrups or suspensions, e.g., solutions containing from about 0.2% by weight to about 20% by weight of the active compound disclosed, and glycerol and propylene glycol. If desired, such preparations can contain colouring agents, flavouring agents, saccharine, and carboxymethyl cellulose as a thickening agent.

The daily dose of the active compound varies and is dependent on the type of administrative route, but as a general rule it is 1 to 100 mg/dose of active compound at peroral administration, and 2 to 200 mg/dose in topical administration. The number of applications per 24 hrs depend of the administration route, but may vary, e.g. in the case of a topical application in the nose from 3 to 8 times per 24 hrs, i.a., depending on the flow of phlegm produced by the body treated in therapeutic use. In prophylactic use the number may be on the lower side of the range given.

The topical form can preferably be used in prophylactic treatment, preferably in connection with an infection caused by a rhinitis virus.

The protein can also be used as an additive in infant food, particularly for prophylactic reasons, in order to supply the casein in an easy way to the child. Infants normally reject pharmaceuticals for different reasons. The food product can thus be in the form of a pulverulent porridge base, gruel base, milk substitute base, or more complex food product as of the Scotch collops type, comprising vegetables and meat pieces, often in disintegrated form.

In the case of protein administration to animals they are normally added to the feedstuffs, which besides the protein contains commonly used nutrients.

In accordance with a further aspect of the invention there is provided a process for determining the presence of *S. neumococci* and *H. influenzae* in a sample taken from the respiratory tract of an animal or human. This process is based on the technique of determining the degree of interaction between the bacteria of the sample and a composition of the present invention. Such interaction may be determined by inhibition or induction of the adherence of the bacteria to cells or other surfaces.

REFERENCES

1. McKenzie, H. A., White, F. H. Jr Adv. Protein Chem. 41:173, 1991
2. Hopper, K. E. and McKenzie, H. A. Biochim. Biophys. Acta 295:352, 1973
3. Schmidt, D. V. and Ebner, K. E. Biochim. Biophys. Acta 263:714, 1972
4. Maynard, F. J. Dairy Res. 59:425, 1992
5. Barman, T. E. Eur. J. Biochim. 37:86, 1973
6. Readhead, K., Hill, T. and Mulloy, B. FEMS Microbiol Lett. 70:969, 1990
7. Gilin, F. D., Reiner, D. S. and Wang, C. S. Science 221:1290, 1983
8. Fiat, A.-M., and Jolles, P. Mol. Cell Biochem. 87:5, 1989
9. Matthews, T. H. J., Nair, C. D. G., Lawrence, M. K. and Tyrrell, D. A. J. Lancet, December, 25:1387, 1976
10. Andersson, B., Dahmén, J., Frejd, T., Leffler, H., Magnusson, G., Noori, G., and Svanborg, C., J. Exp. Med., 158:559, 1983
11. Svanborg, C., Aniansson, G., Mestecky, J., Sabharwal, H., and Wold, A. In Immunology of milk and the neonate, J. Mestecky ed. Plenum Press, New York, 1991
12. Svanborg-Edén, C. and Svennerholm, A.-M., Infect. Immun. 22:790, 1978
13. In Microbial lectins and agglutinins, properties and biological activity, Mirelman, D., Wiley, New York, 1986
14. Andersson, B., Porras, O., Hansson, L. Å., Lagergård, T. and Svanborg-Edén, C. J. Infect. Dis. 153:232, 1986
15. Aniansson, G., Andersson, B., Lindstedt, R., and Svanborg, C., Microbial Pathogenesis 8, 365, 1990
16. Sabharwal, H., Hansson, C., Nilsson, A. K., Saraf, A., L önnerdahl, B., and Svanborg, C. 1993, submitted
17. Lacks, S., and Hotchiss, R. D. Biochim. Biophys. Acta, 38:508, 1960
18. Branefors-Helander, P. Acta Pathol. Microbiol. Immunol. Scand. (B), 80:211, 1972
19. Porras, O., Svanborg Edén, C., Lagergård, T., and Hansson, L. Å. Eur. J. Clin. Microbiol., 4, 310–15, 1985
20. Vanaman, T. C., Brew, K., and Hill, R. L. J. Biol. Chem. 245:4583, 1970
21. Beachey, E. H., J. Infect. Dis. 143, 325, 1981
22. Andersson, B., Beachey, E. H., Tomasz, A., Tuomanen, E., and Svanborg, C., Microbial Pathogenesis, 4, 267, 1988
23. Andersson, B., Eriksson, B., Falsén, E., et al Infect. Immun. 32, 311–17, 1981

What is claimed is:

1. A protein complex obtainable by subjecting casein isolated from human milk by acid precipitation to ion exchange chromatography with an ion exchange material to obtain six fractions using an NaCl gradient, and recovering fraction six as said protein complex.

2. A protein complex according to claim 1, wherein said protein complex comprises moieties of molecular weight 14–15 kD, 30 kD and/or 100 kD.

3. A protein complex according to claim 1, wherein fraction six is recovered at a concentration of NaCl of 1M.

4. A protein complex according to claim 1, wherein the complex inhibits attachment of *S. pneumoniae* to human respiratory tract epithelial cells when tested in vitro.

5. A protein complex according to claim 1, wherein the complex inhibits attachment of *H. influenzae* to human respiratory tract epithelial cells when tested in vitro.

6. A food or feed-stuff comprising a protein complex according to claim 1.

7. A pharmaceutical composition comprising a protein complex according to claim 1 in combination with a pharmaceutically acceptable carrier.

8. The pharmaceutical composition according to claim 7, wherein said pharmaceutical composition is in the form of an oral or mucosal dosage unit.

9. The pharmaceutical composition according to claim 7, wherein said pharmaceutical composition is in the form of an injectable composition.

10. The pharmaceutical composition according to claim 7, wherein said pharmaceutical composition is in the form of a topical composition.

11. A method of therapeutically or prophylactically treating a bacterial infection, which method comprises applying to said infection a dose effective to treat said infection of a protein complex according to claim 1.

12. The method according to claim 11 wherein the bacterial infection is in the respiratory tract.

13. The method according to claim 11, wherein the bacterial infection is caused by *S. pneumoniae* and/or *H. influenzae*.

* * * * *